United States Patent
Orbay et al.

(10) Patent No.: US 6,440,135 B2
(45) Date of Patent: Aug. 27, 2002

(54) VOLAR FIXATION SYSTEM WITH ARTICULATING STABILIZATION PEGS

(75) Inventors: Jorge L. Orbay; James Leone, both of Miami, FL (US)

(73) Assignee: Hand Innovations, Inc., Miami, FL (US)

( * ) Notice: Subject to any disclaimer, the term of this patent is extended or adjusted under 35 U.S.C. 154(b) by 1 day.

(21) Appl. No.: 09/735,228

(22) Filed: Dec. 12, 2000

Related U.S. Application Data

(63) Continuation-in-part of application No. 09/524,058, filed on Mar. 13, 2000, now Pat. No. 6,364,882, and a continuation-in-part of application No. 09/495,854, filed on Feb. 1, 2000, now Pat. No. 6,358,250.

(51) Int. Cl.[7] ............................................... A61B 17/80
(52) U.S. Cl. ........................................... 606/69; 606/60
(58) Field of Search ........................ 606/60, 69, 70–73; 623/21.12; 411/481, 484

(56) References Cited

U.S. PATENT DOCUMENTS

| ,472,913 A | * | 4/1892 | Taylor | 411/481 |
|---|---|---|---|---|
| 3,645,161 A | * | 2/1972 | Wesker | 411/393 |
| 4,867,144 A | | 9/1989 | Karas | 128/92 |
| 5,006,120 A | | 4/1991 | Carter | 606/69 |
| 5,531,745 A | | 7/1996 | Ray | 606/61 |
| 5,853,413 A | | 12/1998 | Carter | 606/69 |
| 5,879,350 A | | 3/1999 | Sherman | 606/61 |
| 5,968,047 A | | 10/1999 | Reed | 606/76 |
| 5,989,254 A | | 11/1999 | Katz | 606/73 |
| 6,010,503 A | | 1/2000 | Richelsoph | 606/61 |
| 6,022,350 A | | 2/2000 | Ganem | 606/61 |
| 6,053,917 A | | 4/2000 | Sherman | 606/61 |
| 6,221,073 B1 | * | 4/2001 | Weiss et al. | 606/60 |
| 6,283,969 B1 | * | 9/2001 | Grusin et al. | 606/69 |

OTHER PUBLICATIONS www.osteonics.com/osteonics/spine/xia2.html for XiaTM Spinal System for Polyaxial and Monoaxial Spinal Screws, 4 pages.

\* cited by examiner

Primary Examiner—Jeffrey A. Smith
Assistant Examiner—Michael B. Priddy
(74) Attorney, Agent, or Firm—David P. Gordon; David S. Jacobson; Thomas A. Gallagher

(57) ABSTRACT

A volar fixation system includes a T-shaped plate intended to be positioned against the volar side of the radial bone, a plurality of bone screws for securing the plate along an non-fractured portion of the radial bone, and a plurality of bone pegs which extend from the plate and into bone fragments of a Colles' fracture. The plate includes including a plurality of screw holes and a plurality of threaded peg holes. The bone pegs can be articulated through a range of angles within respective peg holes and fixed at a desired angle within the range. For each peg, once the peg has been appropriately positioned within the peg hole, a set screw is threaded into the peg hole and tightened, thereby securing the peg in the selected orientation.

24 Claims, 6 Drawing Sheets

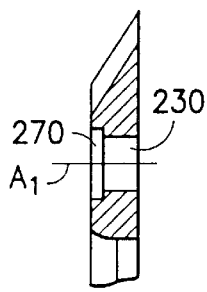 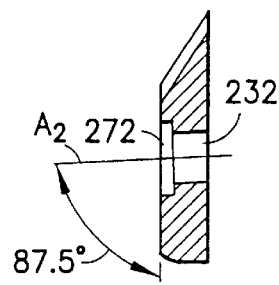 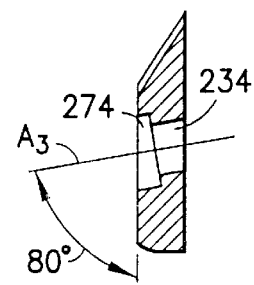 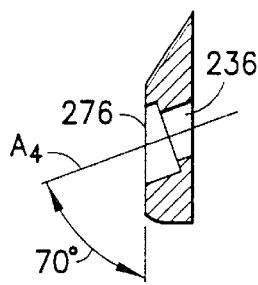
FIG.16   FIG.17   FIG.18   FIG.19
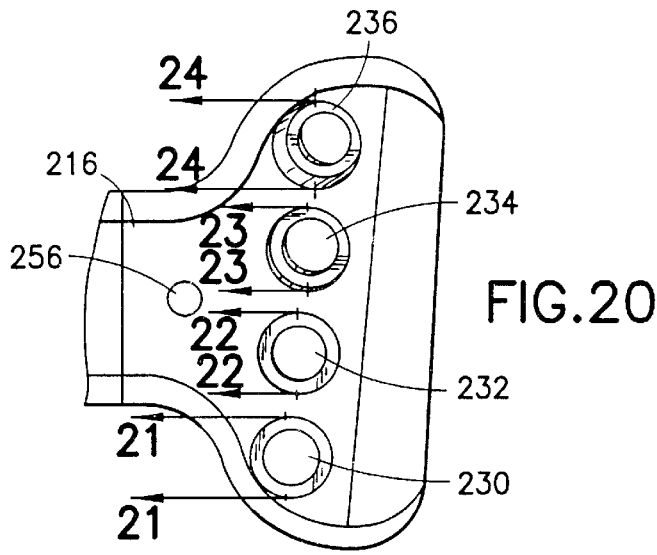
FIG.20
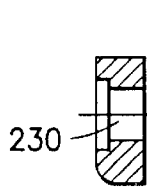 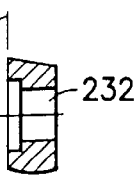 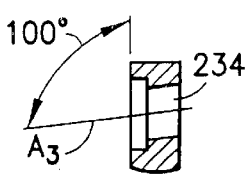 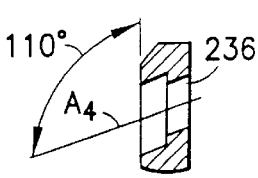
FIG.21   FIG.22   FIG.23   FIG.24

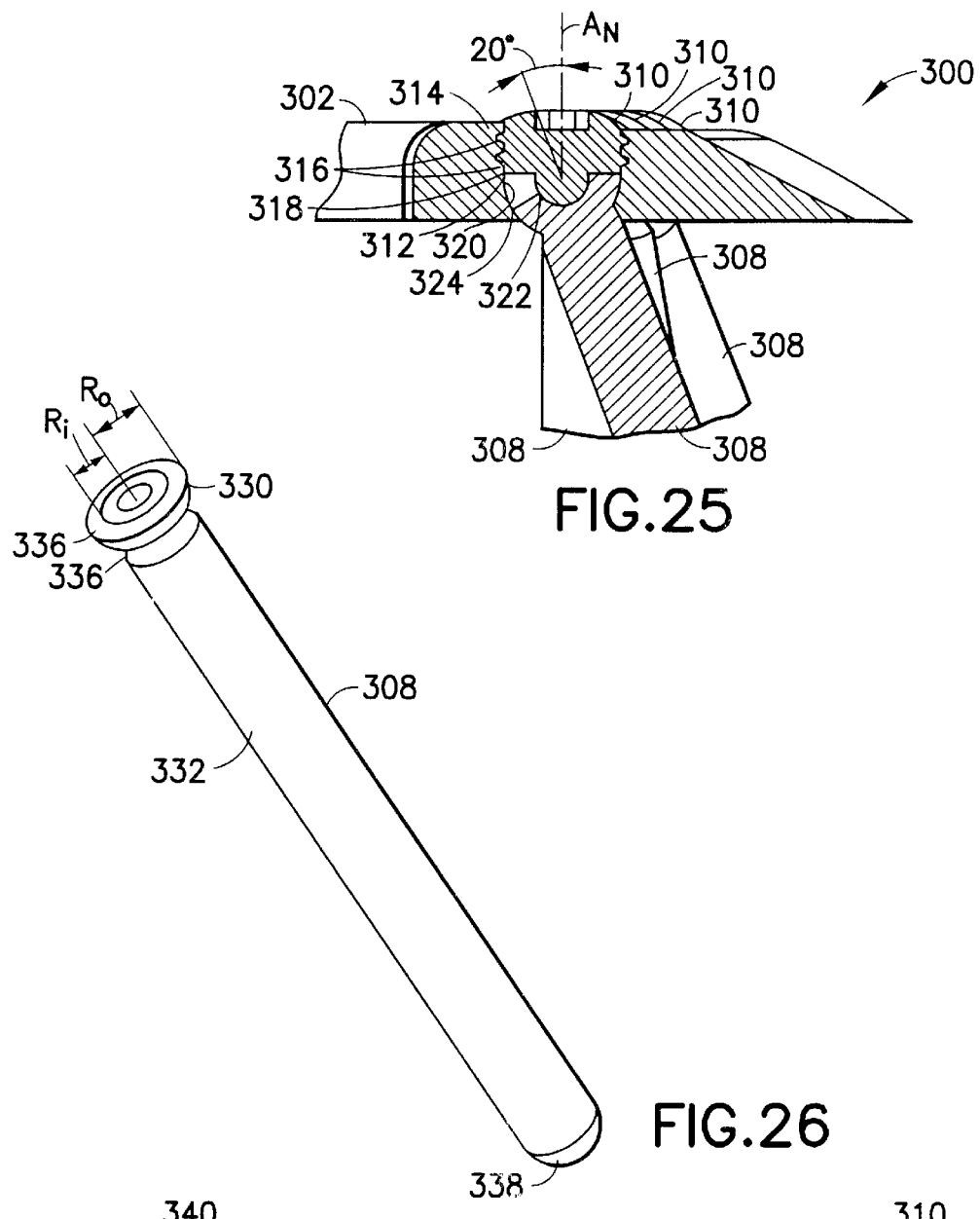
FIG. 25
FIG. 26
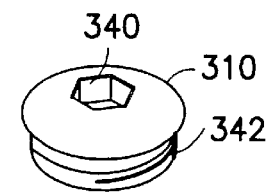
FIG. 27
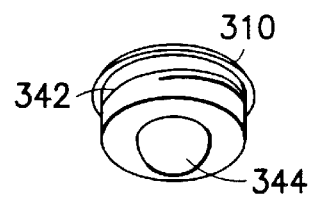
FIG. 28

VOLAR FIXATION SYSTEM WITH ARTICULATING STABILIZATION PEGS

This application is a continuation-in-part of both U.S. Ser. No. 09/524,058, filed Mar. 13, 2000 now U.S. Pat. No. 6,364,882 and U.S. Ser. No. 09/495,854, filed Feb. 1, 2000 now U.S. Pat. No. 6,358,250, which are each hereby incorporated by reference herein in their entireties.

BACKGROUND OF THE INVENTION

1. Field of the Invention

This invention relates broadly to surgical devices. More particularly, this invention relates to a bone fixation system, and particularly to a fixation system adapted to fixate a Colles' (or distal radial) fracture.

2. State of the Art

Referring to FIG. 1, a Colles' fracture is a fracture resulting from compressive forces being placed on the distal radius 10, and which causes backward displacement of the distal fragment 12 and radial deviation of the hand at the wrist 14. Often, a Colles' fracture will result in multiple bone fragments 16, 18, 20 which are movable and out of alignment relative to each other. If not properly treated, such fractures result in permanent wrist deformity. It is therefore important to align the fracture and fixate the bones relative to each other so that proper healing may occur.

Alignment and fixation are typically performed by one of several methods: casting, external fixation, interosseous wiring, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Interosseous wiring is an invasive procedure whereby screws are positioned into the various fragments and the screws are then wired together as bracing. This is a difficult and time consuming procedure. Moreover, unless the bracing is quite complex, the fracture may not be properly stabilized. Plating utilizes a stabilizing metal plate typically against the dorsal side of the bones, and a set of parallel pins extending from the plate into the holes drilled in the bone fragments to provide stabilized fixation of the fragments. However, the currently available plate systems fail to provide desirable alignment and stabilization.

SUMMARY OF THE INVENTION

It is therefore an object of the invention to provide an improved fixation and alignment system for a Colles' fracture.

It is another object of the invention to provide a volar fixation system which desirably aligns and stabilizes multiple bone fragments in a distal radial fracture to permit proper healing.

It is also an object of the invention to provide a volar fixation system which is highly adjustable to provide a customizable framework for bone fragment stabilization.

In accord with these objects, which will be discussed in detail below, a volar fixation system is provided which generally includes a T-shaped plate intended to be positioned against the volar side of the radial bone, a plurality of bone screws for securing the plate along a non-fractured portion of the radial bone, and a plurality of bone pegs which extend from the plate and into bone fragments of a Colles' fracture.

The plate is generally a T-shaped plate defining an elongate body, a head portion angled relative to the body, a first side which is intended to contact the bone, and a second side opposite the first side. The body portion includes a plurality of countersunk screw holes for the extension of the bone screws therethrough. The head portion includes a plurality of threaded peg holes for receiving the pegs therethrough. According to a first embodiment, the peg holes are preferably non-linearly arranged. According to a second embodiment, the peg holes are preferably linearly arranged. In either embodiment, the peg holes are positioned increasingly distal in a medial to lateral direction along the second side. According to a third embodiment, which preferably uses a volar plate with peg holes arranged according to either of the first and second embodiments, the pegs are adjustable relative to the peg holes and can be independently fixed in selectable orientations.

In use, the volar plate is positioned with its first side against the volar side of the radius and bone screws are inserted through the bone screw holes into the radius to secure the volar plate to the radius. The bone fragments are then aligned and the guide plate is positioned on the second side of the volar plate. A drill drills holes into the bone fragments.

The pegs are then inserted through the peg holes and into the holes in the bone. In some embodiments, the heads of the pegs are threadably engaged in the volar plate. In other embodiments, the pegs are inserted into the peg holes and into the drilled holes at an angle chosen by the surgeon, and a set screw is inserted over each peg to lock the peg in the volar plate at the chosen orientation. The volar fixation system thereby stabilizes and secures the bone fragments in their proper orientation.

Additional objects and advantages of the invention will become apparent to those skilled in the art upon reference to the detailed description taken in conjunction with the provided figures.

BRIEF DESCRIPTION OF THE DRAWINGS

FIGS. 16–19 are section views across line 16—16, 17—17, 18—18, and 19—19, respectively in FIG. 15;

FIG. 20 is second partial top view of the head portion of the left hand volar plate according to the second embodiment of the volar fixation system of the invention;

FIGS. 21–24 are section views across line 21—21, 22—22, 23—23, and 24—24, respectively in FIG. 20;

FIG. 25 is a broken partial longitudinal section view across a distal end of a third embodiment of the volar fixation system of the invention;

FIG. 26 is a proximal perspective view of a bone peg according to the third embodiment of the invention; and FIGS. 27 and 28 are proximal and distal perspective views, respectively, of a set screw according to the third embodiment of the invention.

DETAILED DESCRIPTION OF THE PREFERRED EMBODIMENTS

Figure 1:
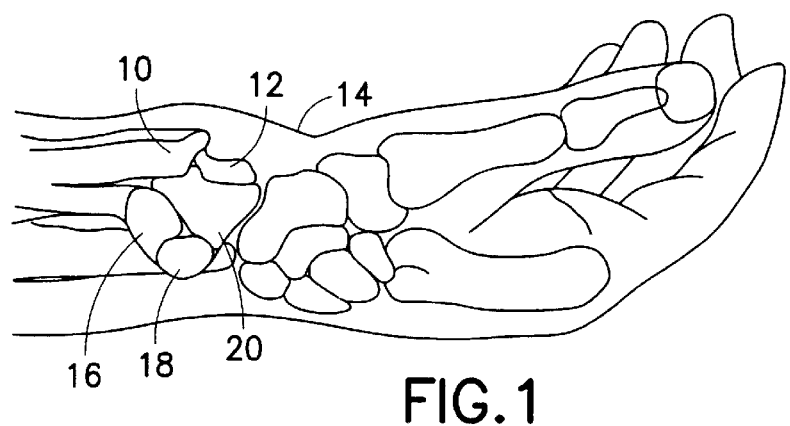
FIG. 1 is an illustration of an extremity subject to a Colles' fracture.
Figure 2:
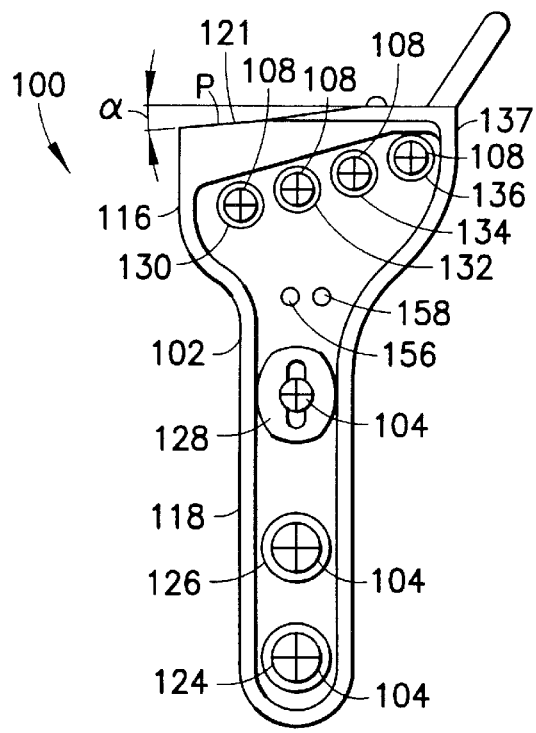
FIG. 2 is a top volar view of a right hand volar fixation system according to a first embodiment of the invention.
Figure 3:
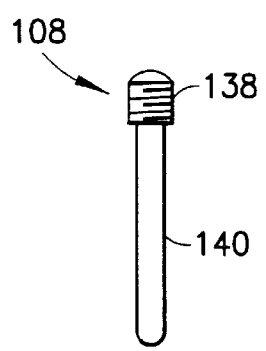
FIG. 3 is a side view of a bone peg according to the first embodiment of the volar fixation system of the invention.
Figure 4:
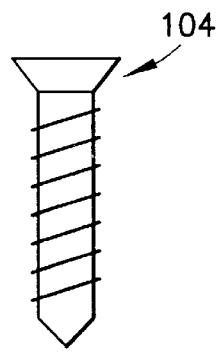
FIG. 4 is a side view of a bone screw of the volar fixation system of the invention.

Turning now to FIGS. 2 through 4, a first embodiment of a volar fixation system 100 for aligning and stabilizing multiple bone fragments in a Colles' fracture generally includes a substantially rigid T-shaped plate 102 intended to be positioned against the volar side of the radial bone, a plurality of preferably self-tapping bone screws 104 for securing the plate 102 along a non-fractured portion of the radial bone, and a plurality of bone pegs 108 which extend from the plate 102 and into bone fragments of a Colles' fracture.

Figure 5:
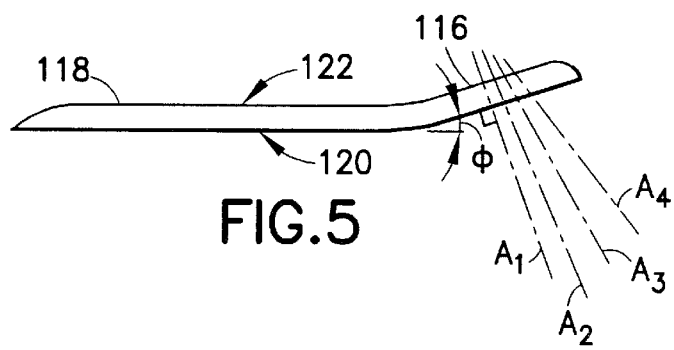
FIG. 5 is a side view of the right hand volar plate of the volar fixation system according to the first embodiment of the invention.
Figure 6:
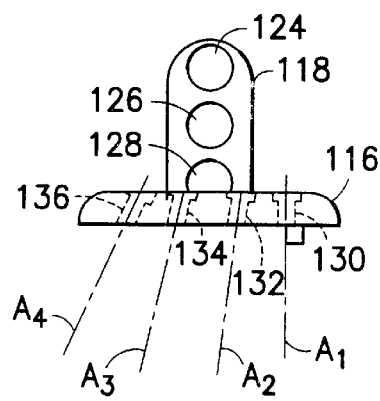
FIG. 6 is a front end view of the right hand volar plate of the volar fixation system according to the first embodiment of the invention.

Referring to FIGS. 2, 5 and 6, more particularly, the T-shaped plate 102 defines a head portion 116, an elongate body portion 118 angled relative to the head portion, a first side 120 which is intended to contact the bone, and a second side 122 opposite the first side. The first side 120 at the head portion is preferably planar, as is the first side at the body portion. As the head portion and body portion are angled relative to each other, the first side preferably defines two planar portions. The angle Ø between the head portion 116 and the body portion 118 is preferably approximately 18° and bent at a radius of approximately 1.00 inch (FIG. 5). The distal edge 121 of the head portion 116 is preferably angled proximally toward the medial side at an angle $\alpha$, e.g., 5°, relative to a line P, which is perpendicular to the body portion. The head portion 116 preferably has a width of 0.913 inch and a greatest proximal-distal dimension (i.e., from the corner of angle $\alpha$ to the body portion) of approximately 0.69 inch, and the body portion preferably has a width of 0.375 inch and a length of 1.40 inches. The plate 102 preferably has a thickness of approximately 0.098 inch. The plate 102 is preferably made from a titanium alloy, such as Ti-6A-4V.

The body portion 118 includes three preferably countersunk screw holes 124, 126, 128 for the extension of the bone screws 104 therethrough. The first screw hole 124 has a center preferably 0.235 inch from the end of the body portion, the second screw hole 126 has a center preferably 0.630 inch from the end of the body portion, and the third screw hole 128 is preferably generally elliptical (or oval) and defines foci-like locations at 1.020 inches and 1.050 inches from the end of the body portion. The head portion 116 includes four threaded peg holes 130, 132, 134, 136 for individually receiving the pegs 108 therethrough. According to a first preferred aspect of the first embodiment of the invention, the peg holes 130, 132, 134, 136, preferably 0.100 inch in diameter, are preferably non-linearly arranged along the head portion 116, and are provided such that the adjacent peg holes are provided further distally in a medial to lateral direction along the second side. More particularly, according to a preferred aspect of the first embodiment of the invention, the peg holes are preferably arranged along a parabolic curve, with the center of peg hole 130 located approximately 0.321 inch proximal line P and approximately 0.719 inch medial of the lateral edge 137 of the head portion, the center of peg hole 132 located approximately 0.296 inch proximal line P and approximately 0.544 inch medial of the lateral edge 137, the center of peg hole 134 located approximately 0.250 inch proximal line P and approximately 0.369 inch medial of the lateral edge 137, and the center of peg hole 136 located approximately 0.191 inch proximal line P and approximately 0.194 inch medial of the lateral edge 137.

In addition, according to a second preferred aspect of the first embodiment of the invention, the peg holes define axes $A_1$, $A_2$, $A_3$, $A_4$ which are oblique (not parallel) relative to each other, and more preferably are angled in two dimensions (medial/lateral and proximal/distal) relative to each other; i.e., the pegs once inserted into the peg holes are also angled in two dimensions relative to each other. More particularly, the first axis $A_1$ of the first peg hole 130 (that is, the most proximal and medial peg hole) is preferably directed normal to the first side 120 of the head portion 116. The axis $A_2$ of the adjacent peg hole 132, i.e., the second axis, is preferably angled approximately 1–7° distal and lateral relative to the first axis $A_1$, and more preferably approximately 2.5° distal and lateral relative to the first axis $A_1$. The axis $A_3$ of the peg hole 134 laterally adjacent the second peg hole 132, i.e., the third axis, is preferably angled approximately 7–13° distal and lateral relative to the first axis $A_1$, and more preferably approximately 10° distal and lateral relative to the first axis $A_1$. The axis $A_4$ of the peg hole 134 laterally adjacent the third peg hole 132, i.e., the fourth axis, is preferably angled approximately 10–30° distal and lateral relative to the first axis $A_1$, and more preferably approximately 20° distal and lateral relative to the first axis $A_1$. The second side of the head portion 116, distal of the peg holes 130, 132, 134, 136 is preferably beveled.

Referring back to FIG. 3, the pegs 108, preferably approximately 0.872 inch in length, each have a threaded head 138 adapted to threadably engage the threads about the peg holes 130, 132, 134, 136, and have a relatively smooth non-threaded cylindrical shaft 140. The shafts 140 are preferably approximately 0.0675 inch in diameter and 0.765 inch in length. Such dimensions permit the pegs to adequately support the bone fragments such that the bone is able to heal correctly. The pegs 108 are also preferably made from titanium alloy, and may be coated in a ceramic, e.g., titanium nitride, to provide a bone interface which will not adversely affect bone healing.

Figure 7:
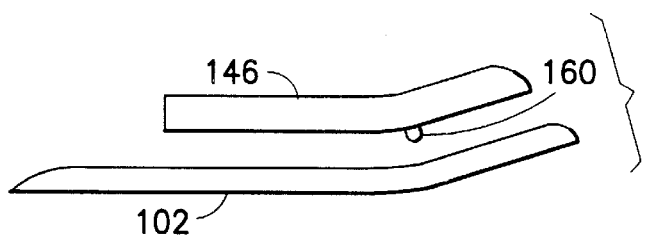
FIG. 7 is an exploded side view of the right hand volar plate and guide plate according to the first embodiment of the fixation system of the invention.
Figure 8:
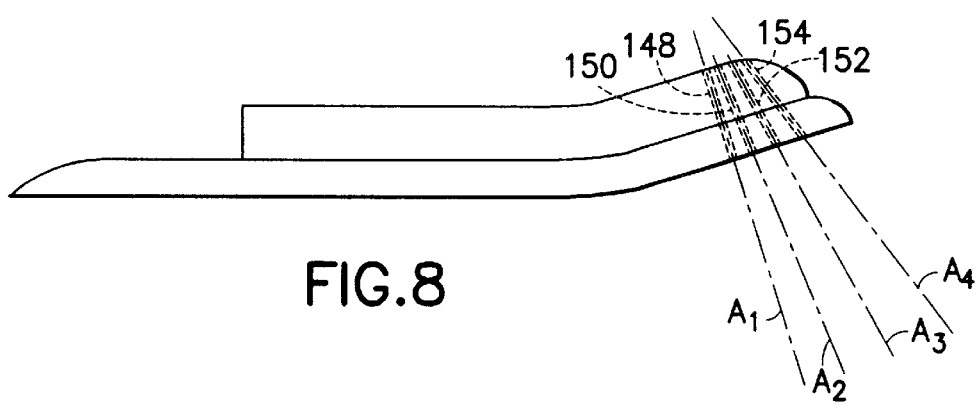
FIG. 8 is a side view of the guide plate positioned on the right hand volar plate to provide drill guide paths in accord with the invention.
Figure 9:
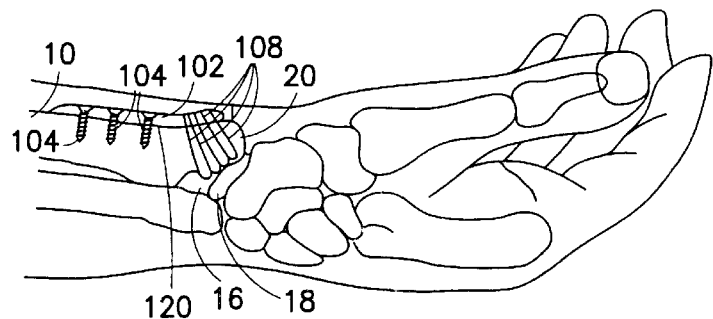
FIG. 9 is an illustration of the first embodiment of the volar fixation system provided in situ aligning and stabilizing a Colles' fracture.

Turning now to FIGS. 7 and 8, the system 100 preferably also includes a guide plate 146 which temporarily sits on the second side 122 of the volar plate 102 and includes guide holes 148, 150, 152, 154 (illustrated in overlapping section in FIG. 8) oriented according to the axes $A_1, A_2, A_3, A_4$ of the peg holes for guiding a drill into the bone fragments at the required orientation. That is, the guide holes together with the peg holes define a drill guide path along the axes with sufficient depth to accurately guide a drill (not shown) to drill holes at the desired pin orientations. The volar plate 102 and guide plate 146 are also preferably provided with mating elements, such as a plurality of holes 156, 158 on the second side of the volar plate (FIG. 2), and a plurality of protuberances 160 on the mating side of the guide plate (FIG. 7), to temporarily stabilize the guide plate on the volar plate during the hole drilling process.

Referring to FIGS. 2 through 9, in use, the volar plate 102 is positioned with its first side 120 against the volar side of the radius. Bone screws 104 (either self-tapping or inserted with the aid of pre-drilled pilot holes) are inserted through the bone screw holes 124, 126, 128 into the radius bone 10 to secure the volar plate 102 to the radius. The bone fragments 16, 18, 20 are then aligned with the radius 10. Next, the guide plate 146 is positioned on the second side of the volar plate. A drill, guided by a guide path formed by the peg holes and the guide holes, drills holes into and between the bone fragments 16, 18, 20 (and possibly also a portion of the integral radius, depending upon the particular location and extent of the fracture), and the guide plate is then removed. The pegs 108 are then inserted through the peg holes 130, 132, 134, 136 and into the holes drilled into the fragments, and the heads of the pegs are threadably engaged in the volar plate. The pegs 108, extending through the oblique-axis peg holes 130, 132, 134, 136, are positioned immediately below the subcondylar bone of the radius and support the bone fragments for proper healing. The volar fixation system thereby secures the bone fragments in their proper orientation.

Figure 10:
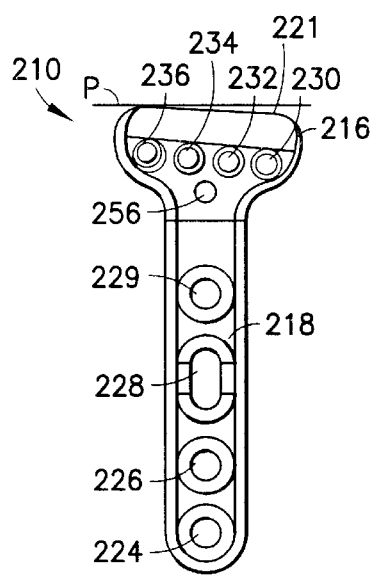
FIG. 10 is a top volar view of a left hand volar fixation system according to the second embodiment of the invention.
Figure 11:
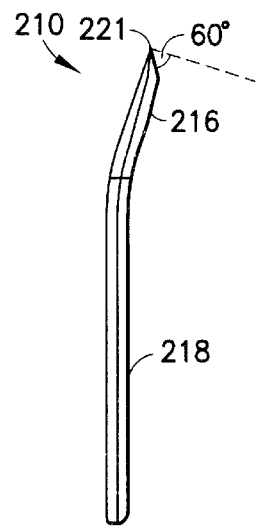
FIG. 11 is a lateral side view of the left hand volar fixation system according to the second embodiment of the invention.
Figure 12:
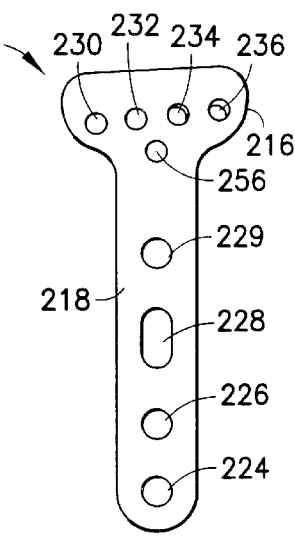
FIG. 12 is a bottom view of the left hand volar fixation system according to the second embodiment of the invention.

Referring to FIGS. 10–12, a second embodiment of a volar plate 210, substantially similar to the first embodiment (with like parts having numbers incremented by 100) and used in substantially the same manner as the first embodiment is shown. The plate 210 preferably has a length of approximately 2.35 inches, which is approximately 0.35 inch greater than in the first embodiment. This additional length accommodates an extra bone screw hole 229 in the body of the volar plate such that the volar plate preferably includes four bone screw holes 224, 226, 228, 229. The additional bone screw in screw hole 229 increases plate stability over the three holes of the first embodiment. The plate 210 preferably tapers in thickness from the body portion 218 to the head portion 216. A preferred taper provides a proximal body portion 218 thickness of approximately 0.098 inch and head portion 216 thickness of approximately 0.078 inch. The taper decreases the thickness of the head portion 216 relative to the body such that the weight of the volar plate is reduced and an improved tendon clearance is provided. The distal edge of the head portion 216 has an increased taper (preferably approximately 60° relative to a line normal to the head) to a distal edge 221. The edge 221 is broken (i.e., made blunt) to prevent irritation or disturbance to the surrounding anatomy.

The head portion 216 includes four threaded peg holes 230, 232, 234, 236 for individually receiving pegs 208 therethrough (FIGS. 13 and 14), and a guide hole 256 for alignment of a guide plate. According to a preferred aspect of the second embodiment of the invention, the peg holes 230, 232, 234, 236, preferably 0.100 inch in diameter, are preferably linearly arranged along the head portion 216, and are provided such that the adjacent peg holes are provided further distally in a medial to lateral direction along the first and second sides. Referring to FIG. 15, more particularly, according to a preferred dimensions of the second embodiment of the invention, the center of peg hole 230 is located approximately 0.321 inch proximal line P and approximately 0.750 inch medial of the lateral edge 237 of the head portion, the center of peg hole 232 is located approximately 0.306 inch proximal line P and 0.557 inch medial of the lateral edge 237, the center of peg hole 234 is located approximately 0.289 inch proximal line P and approximately 0.364 inch medial of the lateral edge 237, and the center of peg hole 236 is located approximately 0.272 inch proximal line P and approximately 0.171 inch medial of the lateral edge 237. As such, the distance from each of the peg holes to the distal edge 221 of the volar plate is relatively greater than in the first embodiment, and provides a preferred alignment with respect to the tapered distal edge 221.

Referring to FIGS. 15–24, in addition, as in the first embodiment, the peg holes define axes $A_1, A_2, A_3, A_4$ which are oblique relative to each other, and more preferably are angled in two dimensions (medial/lateral and proximal/distal) relative to each other; i.e., the pegs 208 once inserted into the peg holes are also angled in two dimensions relative to each other. More particularly, as in the first embodiment, the first axis $A_1$ of the first peg hole 230 is preferably directed normal (FIGS. 16 and 21) to the first side 220 of the head portion 216. The axis $A_2$ of peg hole 232 is preferably angled approximately 1–7° distal (FIG. 17) and approximately 1–7° lateral (FIG. 22) relative to the axis $A_1$, and more preferably approximately 2.5° both distal and lateral relative to axis $A_1$. The axis $A_3$ of peg hole 234 is preferably angled approximately 7–13° distal (FIG. 18) and approximately 7–13° lateral (FIG. 23) relative to axis $A_1$, and more preferably approximately 10° both distal and lateral relative to axis $A_1$. Axis $A_4$ of the peg hole 234 is preferably angled approximately 10–30° distal (FIG. 19) and approximately 10–30° lateral (FIG. 24) relative to axis $A_1$, and more preferably approximately 20° both distal and lateral relative to axis $A_1$.

Referring to FIGS. 13 and 16–19, each of the peg holes has a countersunk portion 270, 272, 274, 276, respectively, for receiving the head 238 of peg 208. Countersunk portions 270, 272 are each preferably approximately 0.030 inch deep and threaded according to the head of the pegs, as described below. Countersunk portion 274 is preferably approximately 0.042 inch deep and likewise threaded. Countersunk portion 276 is preferably approximately 0.056 inch deep and also threaded. The respective depths of the countersunk portions are adapted to better accommodate the heads 238 of the pegs 208 relative to the respective axes of the peg holes.

Figures 13, 14:
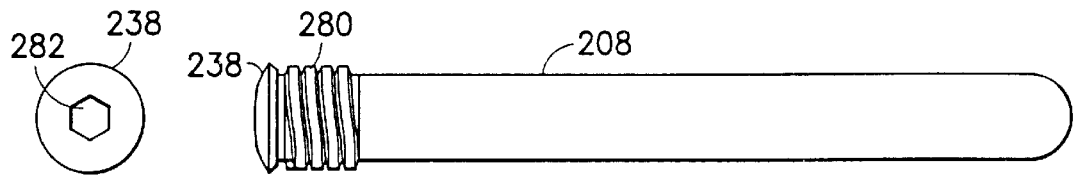
FIG. 13 is an enlarged side elevation of a bone peg according to the second embodiment of the volar fixation system of the invention.
FIG. 14 is a proximal end view of the bone peg of FIG. 13.
Figure 15:
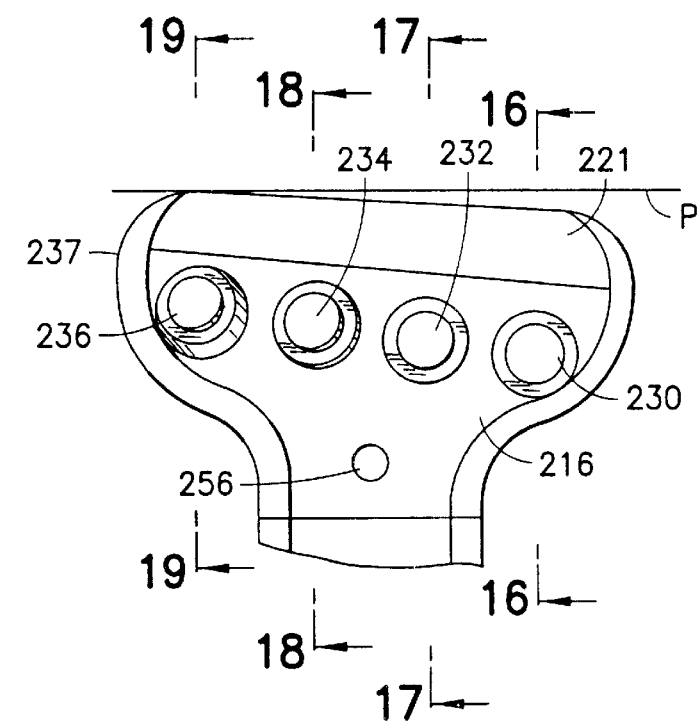
FIG. 15 is first partial top view of the head portion of the left hand volar plate according to the second embodiment of the volar fixation system of the invention.

Referring to FIGS. 13 and 14, the pegs 208, preferably approximately 0.872 inch in length, each have a threaded head 238 adapted to threadably engage threads about the peg holes 230, 232, 234, 236, and have a relatively smooth non-threaded cylindrical shaft 240. The heads 238 preferably include a no. 5 thread 280 at a count of 44 per inch. In addition, the heads 238 are rounded and include a hex socket 282 to facilitate stabilized threading into the peg holes. This design accommodates the reduced thickness of the volar plate at the head portion 216. The shafts 240 are preferably approximately 0.0792 inch (2 mm) in diameter and 0.765 inch in length. Such dimensions permit the pegs to adequately support the bone fragments such that the bone is able to heal correctly. The pegs 208 are also preferably made from titanium alloy, and are preferably 'tiodized' to provide a strong finish which does not adversely affect bone healing.

Turning now to FIG. 25, a volar fixation system 300 according to a third embodiment is shown in which each peg can be articulated through a range of angles within a respective peg hole and fixed at a desired angle within the range. The system includes a volar plate 302, four pegs 308, and four set screws 310, as well as bone screws, not shown but described above, for mounting the volar plate to the radius.

The volar plate 310 is substantially similar to the first or second embodiments, with the exception of the shape of the peg holes described below, and is used in substantially the same manner as the first embodiment. Each peg hole 312 in the volar plate includes a cylindrical upper bore 314 provided with threads 316 and a lower portion 318 having a radius of curvature. The surface 320 of the lower portion and/or the surface 330 of the head of the peg is preferably roughened, e.g., by electrical, mechanical, or chemical abrasion, or by the application of a coating or material having a high coefficient of friction. The lower opening 322 of each peg hole includes a circumferential bevel 324.

Referring to FIGS. 25 and 26, each peg 308 includes a head 330 and a cylindrical shaft 332. The proximal portion 334 of the head 330 includes a cup 336 having an outer radius $R_o$ substantially corresponding to the radius of the lower portion 318 of the peg holes 312, and a relatively smaller inner radius $R_i$ of curvature. The head 330 defines preferably approximately 160° of a sphere. The shaft 332 includes a slight taper 336 at the intersection with the head 330, and a rounded distal end 338. According to a preferred manufacture of the pegs 308, the cylindrical shaft 332 is first provided with a sphere (not shown) or a hemispher (not shown) at a proximal end. If a sphere is provided, it is cut to a hemisphere. The hemisphere is then hollowed and further reduced to the 160° shape. Finally, the taper 336 is provided at the intersection.

Turning now to FIGS. 25, 27 and 28, each set screw 310 includes a proximal hex socket 340, circumferential threads 342 adapted to engage the threads 316 of the upper bore 314 of the peg hole, and distal hemispherical portion 344 having substantially the same radius of curvature as the inner radius of curvature of the cup 336, and preferably substantially smaller than a radius of the peg holes 312.

In accord with the third embodiment, the volar plate is positioned on the radius, a hole is drilled through the elliptical screw hole on the volar plate and into the radius. A bone screw is inserted through the plate and into the bone. The fractured bones are then adjusted under the plate into their desired stabilized positions, and the bone screw is tightened. Then, through the peg holes, the surgeon drills holes into the fracture location for the stabilization pegs. Unlike the previous embodiments, the holes may be drilled at any angle within a predefined range, and preferably at any angle within a range of 20° relative to an axis normal $A_N$ to the lower surface of the head of the volar plate. Each hole may be drilled at the same angle or at relatively different angles. After each hole is drilled, a peg 308 is inserted therein. The bevel 324 at the lower end 322 of the peg hole 312 and the taper 336 on the shaft cooperate to permit the peg to be oriented with greater angularity relative to the axis $A_N$, if required, as interference between the peg hole and peg shaft is thereby reduced. Once the peg 308 has been appropriately positioned within the peg hole, one of the set screws 310 is threaded into the upper bore 314 of the peg hole 312. The hemispherical portion 344 contacts the head 330 of the peg, seating in the concavity of the cup 336. As the set screw 310 is tightened, the head of the peg, which may be roughened, is sandwiched between the set screw and the roughened inner surface of the lower portion of the peg hole, thereby securing the peg in the selected orientation. The other pegs are similarly positioned and angularly fixed.

There have been described and illustrated herein embodiments of a volar fixation system and a method of aligning and stabilizing a Colles' fracture. While particular embodiments of the invention have been described, it is not intended that the invention be limited thereto, as it is intended that the invention be as broad in scope as the art will allow and that the specification be read likewise. Thus, while particular materials for the elements of the system have been disclosed, it will be appreciated that other materials may be used as well. In addition, while a particular number of screw holes in the volar plates and bone screws have been described, it will be understood another number of screw holes and screws may be provided. Further, fewer screws than the number of screw holes may be used to secure to the volar plate to the radius. Also, fewer or more peg holes and bone pegs may be used, preferably such that at least two pegs angled in two dimensions relative to each other are provided. Moreover, while in the first embodiment it is preferred that the peg holes lie along a parabolic curve, it will be appreciated that they can lie along another curve. In addition, while a particular preferred angle between the head portion and body portion has been disclosed, other angles can also be used. Furthermore, while particular distances are disclosed between the peg holes and line P, it will be appreciated that the peg holes may be provided at other distances relative thereto. Moreover, while particular preferred medial/lateral and proximal/distal angles for the peg hole axes has been disclosed, it will be appreciated that yet other angles may be used in accord with the invention. Also, while a right-handed volar plate is described with respect to the first embodiment, and a left-handed volar plate is described with respect to the second embodiment, it will be appreciated that each embodiment may be formed in either a right- or left-handed model, with such alternate models being mirror images of the models described. In addition, while a range of 20° in which the pins may articulate is disclosed, the peg holes and pegs may be modified to permit a greater or smaller range of articulation. Furthermore, while a hex socket is disclosed on the set screws for applying rotational force thereto, it will be appreciated that other rotational engagement means, e.g., a Phillips, slotted, star, rectangular, or other configuration may be used. In addition, aspects from each of the embodiments may be combined. It will therefore be appreciated by those skilled in the art that yet other modifications could be made to the provided invention without deviating from its spirit and scope as claimed.

What is claimed is:

1. A volar fixation system, comprising:
  a) a substantially rigid plate including a distal head portion and a proximal body portion angled relative to said head portion,
    said head portion defining a plurality of peg holes adapted to individually receive fixation pegs therein, said peg holes having an upper portion and a lower portion, said upper portion having a first internal thread, and said lower portion having spherical radius of curvature,
    said body portion including at least one screw hole;
  b) a plurality of pegs each having a head portion and a shaft portion, said shaft portion sized to be received though said peg holes, and said head portion having an outer surface with substantially a same spherical radius of curvature as said lower portion of said peg holes; and c) a plurality of set screws each having a body including a second thread rotationally engageable with said first thread, and a proximal rotational engagement means for engaging said set screw and applying a rotational force thereto, wherein when said pegs are provided into respective peg holes, each said peg may be positioned at any angle within a predefined range of angles relative to an axis normal to a lower surface of said head portion of said plate, and once so positioned, respective set screws threaded into said upper portions of said peg holes fix said pegs in their respective angles.

2. A volar fixation system according to claim 1, wherein:
said predefined range includes 20° relative to said axis normal to said lower surface of said head portion of said plate.

3. A volar fixation system according to claim 1, wherein:
said lower portion of each of said peg holes is processed to have a relatively high coefficient of friction.

4. A volar fixation system according to claim 1, wherein:
said outer surface of said head portion of each of said pegs is processed to have a relatively high coefficient of friction.

5. A volar fixation system according to claim 1, wherein:
said peg holes are linearly arranged.

6. A volar fixation system according to claim 1, wherein:
said head portion defines a medial side and a lateral side, and said peg holes are arranged in a generally medial to lateral direction wherein successive lateral peg holes are situated distally relative to adjacent peg holes.

7. A volar fixation system according to claim 1, wherein:
said peg holes lie along a curve.

8. A volar fixation system according to claim 1, wherein:
said head portion includes exactly four peg holes.

9. A volar fixation system according to claim 1, wherein:
a taper is provided at an intersection of said head and said shaft of each of said pegs.

10. A volar fixation system according to claim 9, wherein:
a bevel is provided about a lower opening of each of said peg holes.

11. A volar fixation system according to claim 1, wherein:
each of said head portions of said pegs is concave, and each of said set screws includes a distal convex portion seating with said concave head portions.

12. A volar fixation system according to claim 11, wherein:
said concave and convex portions are each defined by a substantially same radius.

13. A volar fixation system according to claim 1, wherein:
said outer surface of said head portion defines a shape that is substantially a spherical portion but less than a hemisphere.

14. A volar fixation system according to claim 1, wherein:
said rotational engagement means of each of said set screws is a hex socket.

15. A volar fixation system according to claim 1, wherein:
said shaft portion of each of said pegs is a non-threaded cylinder.

16. A volar fixation plate, comprising:
a substantially rigid T-shaped plate including a distal head portion and a proximal body portion angled relative to said head portion, said head portion defining a plurality of peg holes adapted to individually receive fixation pegs therethrough, said peg holes each having an upper portion and a lower portion, the lower portion having spherical radius of curvature, said body portion including at least one screw hole.

17. A volar fixation plate according to claim 16, wherein:
each said upper portion includes a thread.

18. A volar fixation plate according to claim 16, wherein:
each said lower portion is processed to have a relatively high coefficient of friction.

19. A volar fixation plate according to claim 16, wherein:
said peg holes are linearly arranged.

20. A volar fixation plate according to claim 16, wherein:
said head portion defines a medial side and a lateral side, and said peg holes are arranged in a generally medial to lateral direction wherein successive lateral peg holes are situated distally relative to adjacent peg holes.

21. A volar fixation plate according to claim 16, wherein:
said peg holes lie along a curve.

22. A volar fixation plate according to claim 16, wherein:
said head portion includes exactly four peg holes.

23. A peg for insertion into a peg hole in a fracture fixation system, comprising:

a) a head having an outer surface with a first substantially spherical radius of curvature and a concavity with a second substantially spherical radius of curvature, said head defining less than a hemisphere; and b) a cylindrical shaft coupled to said head, said shaft including a taper adjacent said head.

24. A peg according to claim 23, wherein:
said outer surface of said head portion is processed to have a relatively high coefficient of friction.

* * * * *